(12) United States Patent
Majeed et al.

(10) Patent No.: US 11,458,117 B2
(45) Date of Patent: Oct. 4, 2022

(54) COMPOSITIONS AND METHODS FOR BETA SECRETASE INHIBITION

(71) Applicants: Muhammed Majeed, Edison, NJ (US); Kalyanam Nagabhushanam, East Windsor, NJ (US)

(72) Inventors: Muhammed Majeed, Edison, NJ (US); Kalyanam Nagabhushanam, East Windsor, NJ (US)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/008,219

(22) Filed: Jun. 14, 2018

(65) Prior Publication Data
US 2018/0360800 A1    Dec. 20, 2018

Related U.S. Application Data

(60) Provisional application No. 62/520,141, filed on Jun. 15, 2017.

(51) Int. Cl.
| | | |
|---|---|---|
| *A61K 31/352* | (2006.01) | |
| *A61P 27/06* | (2006.01) | |
| *A61P 25/28* | (2006.01) | |
| *A61P 25/16* | (2006.01) | |
| *A61K 36/185* | (2006.01) | |
| *A61P 39/00* | (2006.01) | |
| *A61K 31/353* | (2006.01) | |
| *A61K 9/00* | (2006.01) | |

(52) U.S. Cl.
CPC .......... *A61K 31/352* (2013.01); *A61K 31/353* (2013.01); *A61K 36/185* (2013.01); *A61P 25/16* (2018.01); *A61P 25/28* (2018.01); *A61P 27/06* (2018.01); *A61P 39/00* (2018.01); *A61K 9/0053* (2013.01)

(58) Field of Classification Search
CPC ..... A61K 31/352; A61K 9/0053; A61P 25/16; A61P 25/28; A61P 27/06
USPC ....................................................... 514/456
See application file for complete search history.

(56) References Cited

U.S. PATENT DOCUMENTS

| | | | | |
|---|---|---|---|---|
| 7,514,469 B2 * | 4/2009 | Jia | .......................... | A61K 31/35 514/456 |
| 7,674,830 B2 * | 3/2010 | Jia | .......................... | A61K 31/35 514/732 |
| 8,034,387 B2 * | 10/2011 | Jia | .......................... | A61K 31/353 424/725 |
| 8,945,518 B2 * | 2/2015 | Jia | .......................... | A61K 31/353 424/50 |
| 2005/0096281 A1 * | 5/2005 | Jia | .......................... | A61K 31/35 514/27 |

OTHER PUBLICATIONS

Tong et al. (vol. 70, Nov. 2012, pp. 6-12. Journal of Pharmaceutical and Biomedical Analysis).*
Chaudhary et al., Current Therapeutic Targets for Alzheimer's Disease, Journal of Biomedicine, 2018; 3: 74-84. doi: 10.7150/jbm.26783.
Zhang et al., NSAID Exposure and Risk of Alzheimer's Disease: An Updated Meta-Analysis From Cohort Studies, Some aspects of chemotaxonomy, Front Aging Neurosci. 2018; 10: 83.
Wang et al.,, Anti-Inflammatory Drugs and Risk of Alzheimer's Disease: An Updated Systematic Review and Meta-Analysis, J Alzheimers Dis. 2015;44(2):385-96.
Jordan et al., Aspirin and other non-steroidal anti-inflammatory drugs for the prevention of dementia. Cochrane Database of Systematic Reviews 2020, Issue 4. Art. No.: CD011459. DOI: 10.1002/14651858.CD011459.pub2.
Vassar et al., The β-Secretase Enzyme BACE in Health and Alzheimer's Disease: Regulation, Cell Biology, Function, and Therapeutic Potential, J Neurosci. Oct. 14, 2009; 29(41): 12787-12794.
Maia et al., BACE-1 and γ-Secretase as Therapeutic Targets for Alzheimer's Disease, Pharmaceuticals 2019, 12, 41; doi:10.3390/ph12010041.
Chaudhary et al., Current Therapeutic Targets for Alzheimer's Disease, J Biomed 2018; 3:74-84.
Vassar et al., (2009) The β-Secretase Enzyme BACE in Health and Alzheimer's Disease: Regulation, Cell Biology, Function and Therapeutic Potential, J Neurosci.; 29(41): 12787-12794.
Macini et al., (2011) Beta-secretase as a target for Alzheimer's disease drug discovery: an overview of in vitro methods for characterization of inhibitors, Analytical and Bioanalytical Chemistry; 400 (7):1979-1996.
Youn et al., (2017) Polymethoxyflavones: Novel β-Secretase (BACE1) Inhibitors from Citrus Peels, Nutrients; 9(9): 973.
Zang et al., (2013) baicalein reduces β-amyloid and promotes nonamyloidogenic amyloid precursor protein processing in an Alzheimer's disease transgenic mouse model, J Neurosci Res.;91(9):1239-46.

* cited by examiner

Primary Examiner — Sabiha N Qazi

(57) ABSTRACT

Disclosed are the uses of compositions containing not less than 10% w/w of Oroxylin A, not less than 10% w/w of Baicalein and not less than 2% w/w of Chrysin in inhibiting the activity and expression of β secretase. The invention also discloses the reduction of amyloid content in PS-70 cells using the abovementioned composition. Further, the invention mentions the use of the composition for the therapeutic management of β secretase mediated disorders.

3 Claims, 2 Drawing Sheets

COMPOSITIONS AND METHODS FOR BETA SECRETASE INHIBITION

CROSS-REFERENCE TO RELATED PATENT APPLICATION

The present invention is non-provisional filing of U.S. provisional patent application No. 62/520,141 filed on 15 Jun. 2017.

BACKGROUND OF THE INVENTION

Field of the Invention

The invention in general relates to β secretase inhibitors. More specifically the present invention relates to inhibiting the activity and expression of β secretase and reducing β amyloid content using a composition containing oroxylin A, baicalein and chrysin.

Description of Prior Art

Alzheimer's disease is a debilitating disorder of the nervous system characterised by the presence of memory loss, cognitive impairment, disorientation and personality changes. The pathological features include the presence of amyloid plaques and neurofibrillary tangles, leading to inflammation, neuronal damage and apoptosis. There are numerous factors which lead to the development of disease which include oxidative stress, inflammation, diabetes, obesity, elevated blood pressure, genetics, diet, trauma, and the presence of Down's syndrome. Being a multi-factorial disorder, the treatment modalities are concentrated in alleviating one or more symptoms.

A plethora of evidence suggests that β amyloid is central to the pathology of Alzheimer's disease and is likely to play a major role in the disease development. Generated by the action of β site APP cleaving enzyme (BACE, also called as β secretase) on the amyloid precursor protein (APP), these peptides of length 1-42 amino acids, accumulates in the synaptic space and increase the excito-toxicity on the neurons leading to neuronal damage and apoptosis. The role of BACE is well documented in the following prior art documents:

1. Vassar et al., (2009) The β-Secretase Enzyme BACE in Health and Alzheimer's Disease: Regulation, Cell Biology, Function and Therapeutic Potential, J Neurosci.; 29(41): 12787-12794.
2. Cole and Vassar (2007) The Alzheimer's disease β-secretase enzyme, BACE1, *Molecular Neurodegeneration;* 2:22
3. Macini et al., (2011) Beta-secretase as a target for Alzheimer's disease drug discovery: an overview of in vitro methods for characterization of inhibitors, Analytical and Bioanalytical Chemistry; 400 (7): 1979-1996.
4. Fukumoto et al., (2002) β-Secretase Protein and Activity Are Increased in the Neocortex in Alzheimer Disease, Arch Neurol.; 59(9): 1381-1389.
5. Lange et al., (2015) Association of a BACE1 Gene Polymorphism with Parkinson's disease in a Norwegian Population, Parkinsons Dis.; 2015: 973298.

Apart from its role in neurodegenerative diseases, BACE1 is also reported to play a role in the development of glaucoma (Guo et al., (2007) Targeting amyloid-β in glaucoma treatment, Proc Natl Acad Sci USA; 104(33): 13444-13449).

Inhibiting the activity and expression of β secretase would be an effective option to alleviate the symptoms of β secretase related disorders like Alzheimer's disease, Parkinson's disease, Prion related diseases, cognitive decline, mild cognitive impairment, vascular dementia, Down's syndrome, Hereditary cerebral hemorrhage with amyloidosis dutch type (HCHWA-D) and glaucoma. Natural molecules that can inhibit the activity of β secretase are now being increasingly examined. Some of the natural molecules that are reported have β secretase inhibiting activity are indicated in the following prior art documents:

1. Zang and Tanzi (2012) Natural Modulators of Amyloid-Beta Precursor Protein Processing, Curr Alzheimer Res. 2012 PMID: 22998566.
2. Youn et al., (2017) Polymethoxyflavones: Novel β-Secretase (BACE1) Inhibitors from Citrus Peels, Nutrients; 9(9): 973.
3. Fang et al., (2017) β-Secretase (BACE1) Inhibitors from Natural Products, In: Natural Products Targeting Clinically Relevant Enzymes, ed: Paula B. Andrade, Patricia Valentão, David M. Pereira, Wiley Publishers,
4. Zang et al., (2013) baicalein reduces 3-amyloid and promotes nonamyloidogenic amyloid precursor protein processing in an Alzheimer's disease transgenic mouse model, J Neurosci Res.; 91(9):1239-46.

However, a natural molecule and/or a combination of natural molecules that are effective in inhibiting both the expression and activity of β secretase are lacking. The present invention solves the above problem by disclosing a composition containing oroxylin A, baicalein and chrysin for inhibiting the activity and expression of β secretase.

The principle objective of the invention is to disclose the use of a composition containing oroxylin A, baicalein and chrysin for inhibiting the activity and expression of β secretase.

It is another objective of the invention to disclose the use of a composition containing oroxylin A, baicalein and chrysin for reducing β amyloid content.

It is another objective of the invention to disclose a method of therapeutic management of β secretase mediated disorders using a composition containing oroxylin A, baicalein and chrysin.

The invention fulfils the above mentioned objectives and provides further related advantages.

SUMMARY OF THE INVENTION

The present invention discloses the use of a composition containing not less than 10% w/w of oroxylin A, not less than 10% w/w of baicalein and not less than 2% w/w of chrysin for inhibiting the activity and expression of β secretase. The invention also discloses the reduction of amyloid content in PS-70 cells using the abovementioned composition. Further, the invention mentions the use of the composition for the therapeutic management of β secretase mediated disorders.

DESCRIPTION OF THE MOST PREFERRED EMBODIMENTS

Figure 1:
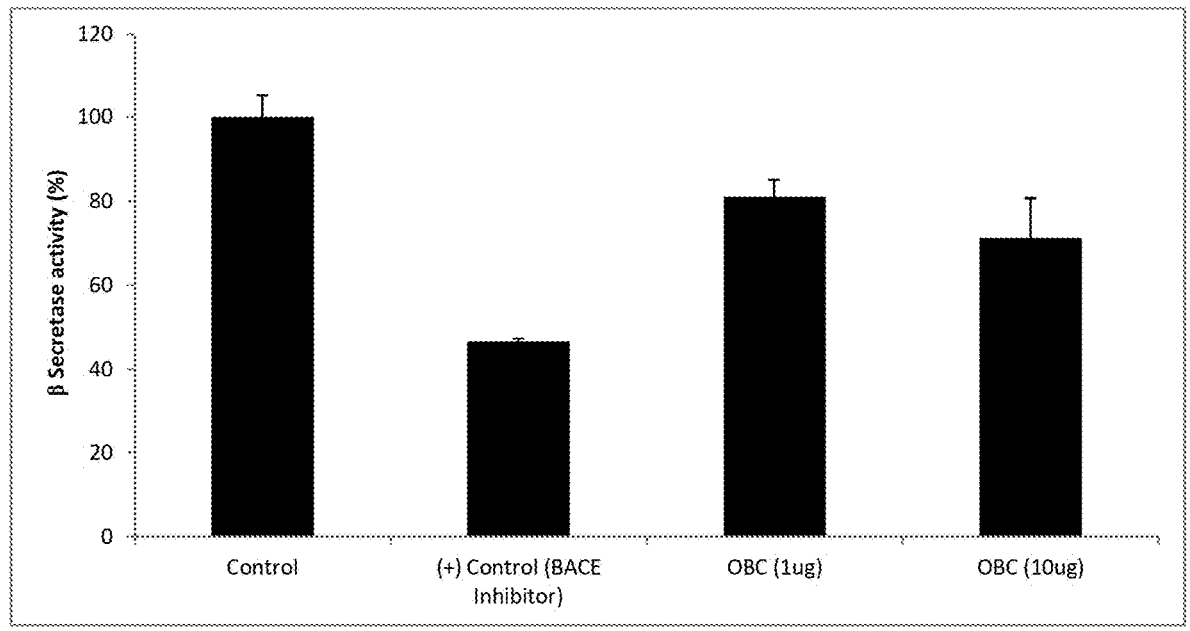
FIG. 1 is a graphical representation for the inhibition of β secretase activity by the composition containing oroxylin A, baicalein and chrysin.

In the most preferred embodiment, the invention discloses a method of inhibiting the activity of β secretase enzyme, said method comprising step of bringing in to contact mammalian cells with a composition containing not less than 10% w/w of oroxylin A, not less than 10% w/w of baicalein and not less than 2% w/w of chrysin, to bring about the effect of inhibiting β secretase activity. In a related embodiment, the composition preferably comprises 10%-15% w/w of oroxylin A, 10%-25% w/w of baicalein and 2%-10% w/w of chrysin.

In the most preferred embodiment, the invention discloses a method of inhibiting the expression of β secretase, said method comprising step of bringing in to contact mammalian cells with a composition containing not less than 10% w/w of oroxylin A, not less than 10% w/w of baicalein and not less than 2% w/w of chrysin, to bring about the effect of reducing the expression of β secretase enzyme. In a related embodiment, the composition preferably comprises 10%-15% w/w of oroxylin A, 10%-25% w/w of baicalein and 2%-10% w/w of chrysin.

In the most preferred embodiment, the invention discloses a method of reducing the β amyloid content, said method comprising step of bringing in to contact mammalian cells with a composition containing not less than 10% w/w of oroxylin A, not less than 10% w/w of baicalein and not less than 2% w/w of chrysin, to reduce the amount of β amyloid. In a related embodiment, the composition preferably comprises 10%-15% w/w of oroxylin A, 10%-25% w/w of baicalein and 2%-10% w/w of chrysin.

In the most preferred embodiment, the invention discloses a method for the therapeutic management of β secretase mediated disorders in mammals, said method comprising step of administering an effective dose of a composition containing not less than 10% w/w of oroxylin A, not less than 10% w/w of baicalein and not less than 2% w/w of chrysin to mammals in need of such therapy. In a related embodiment, the composition preferably comprises 10%-15% w/w of oroxylin A, 10%-25% w/w of baicalein and 2%-10% w/w of chrysin. In another related embodiment, the β secretase mediated disorders are selected from the group consisting of Alzheimer's disease, Parkinson's disease, Prion related diseases, cognitive decline, mild cognitive impairment, vascular dementia, Down's syndrome, Hereditary cerebral haemorrhage with amyloidosis dutch type (HCHWA-D), and glaucoma. In a preferred embodiment, the mammal is human. In another preferred embodiment, the composition is formulated with pharmaceutically/nutraceutically acceptable excipients, adjuvants, diluents or carriers and administered orally in the form of tablets, capsules, syrups, gummies, powders, suspensions, emulsions, chewables, candies and eatables.

The specific examples included herein below illustrate the aforesaid most preferred embodiments of the present invention.

Example 1: Effects of Composition Containing Oroxylin A, Baicalein and Chrysin (OBC) on Beta-Secretase Activity and Expression The composition containing oroxylin A, baicalein and chrysin (OBC), was isolated from *Oroxylum indicum* as per the process mentioned in U.S. patent application Ser. No. 15/805,320.

Methodology: The composition (1 μg and 10 μg) was incubated with PS-70 cells for 24 hours (2 separate treatments). Beta-secretase activity was measured using the commercial fluorimetric kit purchased from Biovision (Catalog #K360-100). Standardized and established western blot procedure was used to study the protein expression of Beta-secretase. β-actin was used as a loading control. Band intensity was calculated by densitometric analysis using AlphaView software.

Figure 2:
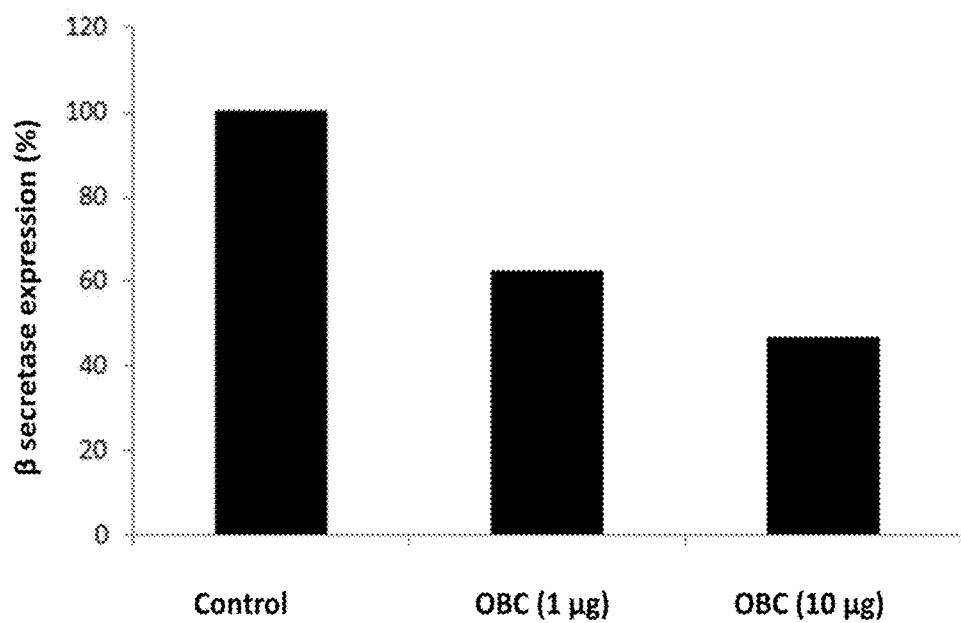
FIG. 2 is a graphical representation for the inhibition of β secretase expression by the composition containing oroxylin A, baicalein and chrysin.
Figure 3:
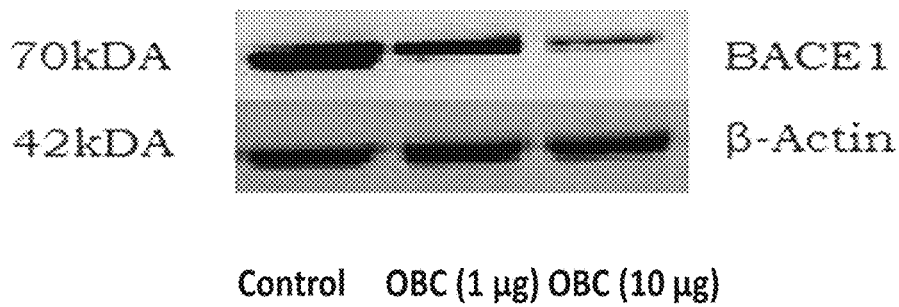
FIG. 3 is western blot image showing the decrease in expression of a β secretase by the composition containing oroxylin A, baicalein and chrysin, compared to control

Results: The composition (1 μg and 10 μg) dose dependently inhibited the beta-secretase activity (FIG. 1) (p<0.0003) and protein expression (FIG. 2) as compared to the control. The western blot image (FIG. 3) also confirms the above indicating that the composition containing oroxylin A, baicalein and chrysin can we effectively used to treat BACE 1 mediated disorders.

Apart from its role in Alzheimer's disease, BACE1 related pathogenesis is also implicated in vascular dementia (Cole and Vassar (2009). Linking vascular disorders and Alzheimer's disease: Potential involvement of BACE1, Neurobiol Aging; 30(10): 1535-1544), Parkinson's disease (Lange et al., (2015) Association of a BACE1 Gene Polymorphism with Parkinson's Disease in a Norwegian Population, Parkinsons Dis.; 2015: 973298), Prion diseases (Parkin et al., (2007) Cellular prion protein regulates β-secretase cleavage of the Alzheimer's amyloid precursor protein, PNAS; 104 (26):11062-11067), cognitive decline, mild cognitive impairment, Down's syndrome, Hereditary cerebral hemorrhage with amyloidosis dutch type (HCHWA-D) (U.S. Pat. No. 9,526,727, Inhibitors of beta-secretase), and glaucoma (Guo et al., (2007) Targeting amyloid-β in glaucoma treatment, Proc Natl Acad Sci USA; 104(33): 13444-13449).

Example 2: Effects of Composition Containing Oroxylin A, Baicalein and Chrysin (OBC) on Beta-Amyloid Content The composition containing oroxylin A, baicalein and chrysin (OBC), was isolated from *Oroxylum indicum* as per the process mentioned in U.S. patent application Ser. No. 15/805,320.

Methodology: The composition (25 μg, 50 μg and 100 μg) was incubated with PS-70 cells for 24 hours. Beta-amyloid content was measured using the commercial beta-amyloid Elisa kit. Beta-amyloid standard curve was done initially and the content was measure after incubation. Pioglitazone (5 and 10 uM) was used as a positive control.

Figure 4:
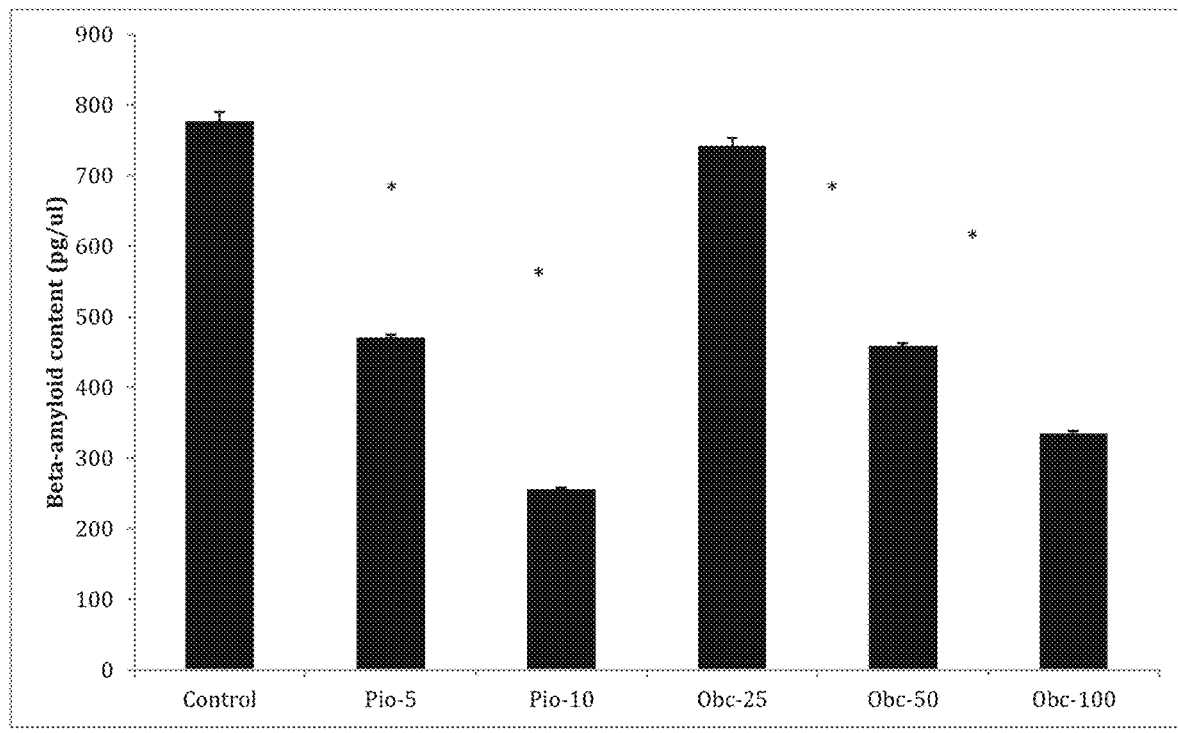
FIG. 4 is a graphical representation showing reduction in amyloid content by the composition containing oroxylin A, baicalein and chrysin. Significantly different from control P<0.001

Results: The composition (25 μg, 50 μg and 100 μg) dose-dependently reduced the beta-amyloid content (p<0.0001) (FIG. 4). Our results were further validated by the use of pioglitazone in this study.

In conclusion, the composition containing oroxylin A, baicalein and chrysin was very effective in inhibiting the activity and expression of β secretase enzyme and also in reducing the amyloid content indicating that the composition may be effectively administered to counter the symptoms associated with β secretase mediated disorders.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of inhibiting the activity of β secretase enzyme, said method comprising step of bringing in to contact mammalian cells with a composition consisting of 10%-15% w/w of oroxylin A, 10%-25% w/w of baicalein and 2%-10% w/w of chrysin, to bring about the effect of inhibiting β secretase activity.

2. A method of inhibiting the expression of β secretase, said method comprising step of bringing in to contact mammalian cells with a composition consisting of 10%-15% w/w of oroxylin A, 10%-25% w/w of baicalein and 2%-10% w/w of chrysin, to bring about the effect of decreasing the expression of β secretase enzyme.

3. A method of reducing β amyloid content, by inhibiting the activity and expression of β secretase, said method comprising step of bringing into contact mammalian cells with a composition consisting of 10%-15% w/w of oroxylin A, 10%-25% w/w of baicalein and 2%-10% w/w of chrysin, to reduce the amount of β amyloid.

* * * * *